United States Patent [19]

Ackerman et al.

[11] Patent Number: 5,242,807
[45] Date of Patent: Sep. 7, 1993

[54] RECOMBINANT GENE ENCODING HUMAN CHARCOT-LEYDEN CRYSTAL PROTEIN

[75] Inventors: Steven J. Ackerman, Sharon; Helene F. Rosenberg, Brighton; Daniel G. Tenen, Boston, all of Mass.

[73] Assignee: Beth Israel Hospital Association, Boston, Mass.

[21] Appl. No.: 430,501

[22] Filed: Nov. 1, 1989

[51] Int. Cl.$^5$ .................... C07H 21/04; C12N 9/14; C12N 15/55; C12N 15/66

[52] U.S. Cl. .................. 435/69.1; 435/69.6; 435/172.3; 435/197; 435/252.3; 435/320.1; 536/23.2

[58] Field of Search ............. 435/69.1, 69.6, 172.3, 435/6, 91, 320.1, 197, 252.3; 935/18, 19, 77, 78, 80; 536/23.2

[56] References Cited

U.S. PATENT DOCUMENTS 4,394,443  7/1983  Weissman et al. ............... 435/6
4,683,195  7/1987  Mullis et al. ..................... 435/6

OTHER PUBLICATIONS

Zhou et al., J. Leuk. Biol., 52:588–595 (1992).
Zhou et al., Blood, 78(10, Suppl. 1):376a, (Abstract #1496), (1991).
Zhou et al., J. Allergy Clin. Immunol., 89(1, Part 2):297, (Abstract #609), (1992).
Zhou et al., J. Cell. Biol., 115 (3, Part 2):241a, (Abstract #1403), (1991).
Weller, P. F., et al., "Biochemical Characterization of Human Eosinophil Charcot-Leyden Crystal Protein", JBC, 259:15100–15105 (1984).
Jansen, R., et al., "cDNA Cloning Strategies Using PCR:Library Sequencing & Cloning of 5 Ends by Primer Extension", J. Cell. Biochem. Supp., (13 part E), p. 292 (1989).
Ackerman et al., Immunobiology of the Eosinophil, 121–144, T. Yoshida and M. Torisu, eds., Elsevier Science Publishing Co., Inc.
Ackerman et al., Advances in Host Defense Mechanisms, 1:269–293, 1982, John J. Gallin and Anthony S. Fauci, eds., Raven Press, New York.
Tung et al., PCR Technology 99–104, 1989, Henry A. Erlich, ed., Stockton Press.
Friedman et al., Nucleic Acids Research, 16:8718, 1988.
Rasmussen et al., Nucleic Acids Research, 17:3306, 1988.
Dor et al., Am. Rev. Respir. Dis., 130:1072–1077, 1984.

*Primary Examiner*—Robert A. Wax
*Assistant Examiner*—Dian Jacobson
*Attorney, Agent, or Firm*—Fish & Richardson

[57] ABSTRACT

A recombinant DNA molecule consisting of segments of DNA from different genomes which have been joined end-to-end outside of living cells, and the progeny of such a recombinant DNA molecule, which recombinant DNA molecule (1) has the capacity to infect a host cell and to be maintained therein, and (2) comprises a DNA coding sequence selected from the group consisting of:

(a) the CLCP-encoding sequence shown in FIG. 1,
(b) a DNA sequence which hybridizes to the CLCP-encoding sequence shown in FIG. 1, and which encodes a polypeptide which (i) cross-reacts with an antibody to CLCP or to denatured CLCP, (ii) exhibits lysophospholipase activity, and (iii) forms dipyramidal crystals under conditions permitting CLC formation; and
(c) a DNA sequence encoding a polypeptide encoded by any of the foregoing DNA sequences.

9 Claims, 2 Drawing Sheets

```
                1                                              50
                |                                              |
          5' ATTCGGGCAATTCAGAMSASNNNCCCAGAAGGAGACAACAATGTCCCTGCTA       52
                                                      MetSerLeuLeu

100
                                          |
          CCCGTGCCATACACAGAGGCTGCCTCTTTGTCTACTGGTTCTACTGTGACAATC        106
          ProValProTyrThrGluAlaAlaSerLeuSerThrGlySerThrValThrIle

150
                                                 |
          AAAGGGCGACCACTTGTCTGTTTCTTGAATGAACCCATATCTGCAGGTGGATTT        160
          LysGlyArgProLeuValCysPheLeuAsnGluProIleSerAlaGlyGlyPhe

200
                                       |
          CACACTGAGATGAAGGAGGAATCAGACATTGTCTTCCATTTCCAAGTGTGCTTT        214
          HisThrGluMetLysGluGluSerAspIleValPheHisPheGlnValCysPhe

250
                                |
          GGTCGTCGTGTGGTCATGAACAGCCGTGAGTATGGGGCCTGGAAGCAGCAGGTG        268
          GlyArgArgValValMetAsnSerArgGluTyrGlyAlaTrpLysGlnGlnVal

300
                                    |
          GAATCCAAGAATATGCCCTTTCAGGATGGCCAAGAATTTGAACTGAGCATCTCA        322
          GluSerLysAsnMetProPheGlnAspGlyGlnGluPheGluLeuSerIleSer

350
                                 |
          GTGCTGCCAGATAAGTACCAGGTAATGGTCAATGGCCAATCCTCTTACACCTTT        376
          ValLeuProAspLysTyrGlnValMetValAsnGlyGlnSerSerTyrThrPhe

400
                                     |
          GACCATAGAATCAAGCCTGAGGCTGTGAAGATGGTGCAAGTGTGGAGAGATATC        430
          AspHisArgIleLysProGluAlaValLysMetValGlnValTrpArgAspIle

450
                                 |
          TCCCTGACCAAATTTAATGTCAGCTATTTAAAGAGATAACCAGACTTCATGTTG        484
          SerLeuThrLysPheAsnValSerTyrLeuLysArgTer

500
                            |
          CCAAGAATCCCTTCTCTAGGTAACTTGGATTCAAGCCAGCTAACAGCTGATCTT        538

550
                  |
          TTCTCACTTCAATCCTTACTCCTGCTCATTAAAACTTAATTAAACTTAAAAAAAAAA 3' 595
```

FIG. 1

RECOMBINANT GENE ENCODING HUMAN CHARCOT-LEYDEN CRYSTAL PROTEIN

BACKGROUND OF THE INVENTION

This invention relates to the cloning of the gene for Charcot-Leyden crystal protein.

Charcot-Leyden crystals (CLC), first described in 1853 by Charcot and Robin in the spleen and blood of a patient who died of leukemia (Charcot and Robin, C. R. Mem. Soc. Biol. 5:44, 1853), and later by Leyden in the sputum of asthmatics (Leyden, Arch. Pathol. Anat. 54:324, 1872), are distinctive hexagonal, bipyramidal crystals that are classically observed in tissues and secretions from sites of eosinophil-associated inflammatory reactions that include those of asthma and myeloid leukemias, as well as allergic, parasitic, and other diseases (Beeson and Bass, The Eosinophil, In *Problems in Internal Medicine* (Smith, ed), Philadelphia: W. B. Saunders 14:39-42, 1977; Ottesen and Cohen, *Allergy: Principles and Practice* (Middleton et al., ed.), St. Louis: C. V. Mosby 2:584-632, 1978). Although CLC are considered a hallmark of the eosinophil, basophils have also been shown to form CLC in vitro (Ackerman et al., J. Exp. Med. 155:1597, 1982) and in vivo (Dvorak and Ackerman, Lab. Invest. 60:557-567, 1989), and CLC have been identified within human basophil granules by ultrastructural studies (Dvorak and Ackerman, 1989).

Eosinophil CLC are formed by a single, markedly hydrophobic protein (CLCP) of 17,400 daltons (Gleich et al., J. Clin Invest. 57:633-640, 1976; Ackerman et al., J. Immunol. 125:2118-2126, 1980; Weller et al., J. Biol. Chem. 259:15100-15105, 1984) that exhibits lysophospholipase activity (lysolecithin acylhydrolase), catalyzing the deacylation of a single fatty acid from lysophospholipids (Weller et al, J. Biol. Chem. 259:15100-15105, 1984). Chromatographically purified human eosinophil lysophospholipase is immunochemically, physicochemically and enzymatically indistinguishable (identical Michaelis constants) from eosinophil CLCP (Weller et al., 1984), and crystallizes to form hexagonal, bipyramidal crystals of habit identical to CLC.

CLCP comprises the sole protein constituent of both native CLC formed in vivo and CLC prepared in vitro from disrupted eosinophils (Weller et al., J. Immunol. 128:1346-1349, 1982). At ~8.5 pg/cell in eosinophils and 4-6 pg/cell in basophils, CLCP is one of the most prominent constituents of each of these cell types. Ultrastructurally, CLCP has been localized in both the eosinophil and basophil to granule compartments; in the mature eosinophil, CLCP was localized to a large, crystalloid-free "primary" granule population (Dvorak et al., Blood 72:150-158, 1988), while in the basophil, CLCP has been found to be a constituent of the histamine, chondroitin sulfate containing basophil granule (Dvorak and Ackerman, Lab. Invest. 60:557-567, 1989). However, quantitative considerations, measurements of enzyme activity of intact cells, and localization by light microscopy using indirect immunofluorescence suggest additional plasma membrane, nuclear membrane or cytoplasmic sources.

Although CLCP comprises 7-10 percent of total eosinophil cellular protein and possesses lysophospholipase activity, its role in eosinophil and basophil function remains obscure.

SUMMARY OF THE INVENTION

In general, the invention features, in one aspect, a recombinant DNA molecule consisting of segments of DNA from different genomes which have been joined end-to-end outside of living cells, and the progeny of such a recombinant DNA molecule, which recombinant DNA molecule (1) has the capacity to infect a host cell and to be maintained therein, and (2) comprises a DNA coding sequence selected from the group consisting of:
 (a) the CLCP-encoding sequence shown in FIG. 1,
 (b) a DNA sequence which hybridizes to the CLCP-encoding sequence shown in FIG. 1, under hybridization conditions of equivalent stringency to those described by Maniatis et al. (in *Molecular Cloning: A Laboratory Manual*, Cold Spring Harbor Laboratory, Cold Spring Harbor, N.Y., 1982, p. 320, 321-4) for the hybridization of a cDNA probe, and which encodes a polypeptide which (i) cross-reacts with an antibody to CLCP or to denatured CLCP, (ii) exhibits lysophospholipase activity when assayed in accordance with the method of Weller et al., 1984, or (iii) forms dipyramidal crystals under conditions described by Ackerman et al., 1980; Sieker et al., J. Mol. Biol. 204:489-491, 1988; or Weller et al., 1980 as permitting formation of CLC.
 (c) a DNA sequence encoding a polypeptide encoded by any of the foregoing DNA sequences.

In preferred embodiments, the recombinant DNA molecule is a plasmid, a phage, or a virus, and further includes an expression control sequence operatively linked to the DNA coding sequence, which DNA coding sequence comprises the CLCP-encoding sequence shown in FIG. 1.

In another aspect, the invention features a unicellular host transformed with a recombinant DNA molecule consisting of segments of DNA from different genomes which have been joined end-to-end outside of living cells, and the progeny of such a molecule, which recombinant DNA molecule (1) has the capacity to infect a host cell and to be maintained therein, and (2) comprises a DNA coding sequence selected from the group consisting of:
 (a) the CLCP-encoding sequence shown in FIG. 1,
 (b) a DNA sequence which hybridizes to the CLCP-encoding sequence shown in FIG. 1 under the hybridization conditions specified above, and which encodes a polypeptide which (i) cross-reacts with an antibody to CLCP or to denatured CLCP, (ii) exhibits lysophospholipase activity, or (iii) forms dipyramidal crystals under conditions described by Ackerman et al., 1980; Sieker et al., 1988; or Weller et al., 1980, as permitting formation of CLC; and
 (c) a DNA sequence encoding a polypeptide encoded by any of the foregoing DNA sequences.

Preferably, the host is selected from the group consisting of strains of *E.coli*, Pseudomonas, *Bacillus subtilis*, *Bacillus stearothermophilus*, other bacilli, yeasts, other fungi, and cultured cells from human, animal or plant tissues.

In another aspect the invention features a substantially pure DNA sequence selected from the group consisting of:
 (a) the CLCP-encoding sequence shown in FIG. 1,
 (b) a DNA sequence which hybridizes to the CLCP-encoding sequence shown in FIG. 1 under the hybridization conditions specified above, and which encodes a polypeptide which (i) cross reacts with an antibody to CLCP or to denatured CLCP, (ii) exhibits lysophospholipase activity, or (iii) forms dipyramidal crystals under conditions described by Ackerman et al., 1980; Sieker et al., 1988; or Weller et al., 1980, as permitting formation of CLC; and (c) a DNA sequence encoding a polypeptide encoded by any of the foregoing DNA sequences.

In another aspect, the invention features a vector (defined as a DNA molecule capable of entering a host cell and being replicated therein) which contains a DNA sequence that encodes CLCP.

In another aspect the invention features a method for producing a polypeptide, which method comprises:

(1) preparing a recombinant DNA molecule consisting of segments of DNA from different genomes which have been joined end-to-end outside of living cells, and the progeny of such a recombinant DNA molecule, which recombinant DNA molecule (a) has the capacity to infect a host cell and to be maintained therein, (b) comprises a DNA coding sequence selected from the group consisting of: (i) the CLCP-encoding sequence shown in FIG. 1, (ii) a DNA sequence which hybridizes to the CLCP-encoding sequence shown in FIG. 1 under the hybridization conditions specified above, and which encodes a polypeptide which (A) cross-reacts with an antibody to CLCP or to denatured CLCP, (B) exhibits lysophospholipase activity, or (C) forms dipyramidal crystals under conditions described by Ackerman et al., 1980; Sieker et al., 1988; or Weller et al., 1980, as permitting formation of CLC; and (iii) a DNA sequence encoding a polypeptide encoded by any of the foregoing DNA sequences, and (c) further comprises an expression control sequence operatively linked to the DNA coding sequence;

(2) transforming an appropriate host with the recombinant DNA molecule;

(3) culturing the host; and (4) collecting the polypeptide.

In preferred embodiments, the host is selected from the group consisting of strains of *E.coli*, Pseudomonas, *Bacillus subtilis*, *Bacillus stearothermophilus*, other bacilli, yeasts, other fungi, and cultured cells from human, animal or plant tissues; and the recombinant DNA molecule is a plasmid, a phage, or a virus.

In another aspect, the invention features a method of isolating from the cDNA library a desired cDNA encoding the entire amino acid sequence of a target polypeptide, which method comprises (a) providing a first single-stranded oligodeoxyribonucleotide primer (i.e., a segment of DNA complementary to a given DNA sequence which, if hybridized to such sequence, is able to serve as the starting point for enzymatically catalyzed DNA synthesis in a 5' to 3' direction, utilizing such DNA sequence as template) comprising a non-poly dT sequence identical to a portion of the DNA sequence located on one strand (the "first strand", which may be either the sense strand [the strand complementary to the mRNA for the polypeptide] or the antisense strand) of the desired cDNA between (i) the 5' end of the first strand of the desired cDNA, and (ii) the region of the desired cDNA which encodes the target polypeptide;

(b) providing a second single-stranded oligodeoxyribonucleotide primer comprising a DNA sequence identical to the sequence of a portion of the vector-specific DNA from the DNA strand (the "second strand") having an orientation opposite (i.e., antiparallel) to that of the first strand, provided that the selected portion of vector-specific DNA is located near enough to the insertion site to permit amplification of the desired cDNA by Polymerase Chain Reaction (PCR) using the first and second primers (That is, the sequence of the second primer is chosen such that it is identical to a segment of second strand vector DNA 5' to the cDNA second strand; on a circular molecule, this segment could be located anywhere along the vector second strand, as long as the length of the DNA sequence to be amplified between the two primers is within the limits of the PCR technique.);

(c) combining the first and second primers with a sample of DNA from the cDNA library under conditions permitting PCR to occur with the desired cDNA as template; and (d) isolating the desired cDNA from the products of the PCR, preferably by a separation procedure comprising electrophoresis on an agarose gel, which is more preferably followed by elution, from the gel, of the band corresponding to the desired cDNA.

The recombinant DNA molecule of the invention will permit the synthesis of large quantities of CLCP in cultured cells, and the protein so produced will be highly consistent from batch to batch. In addition, the entire sequence of CLCP has been deduced by sequencing the cDNA of the invention. Unlike direct protein sequencing by a technique such as Edman degradation, decoding the DNA sequence of a cloned cDNA gene provides an unambiguous and reliable determination of the amino acid sequence of the encoded protein. If a sequence which is not 100% correct is relied upon, for example, to synthesize by chemical methods the polypeptide (or a gene encoding the polypeptide, which gene is then cloned and expressed), the resulting protein may lack the natural protein's biological activity due to incorrect folding or a dysfunctional active site, or, in the case of the synthetic gene, the transcriptional or translational product may be degraded by cellular enzymes as soon as it is produced.

The method disclosed herein of obtaining a cDNA encoding an entire target polypeptide represents an efficient and cost effective method for rapid simultaneous screening of multiple cDNA libraries for isolation of full-length cDNA, as it replaces the multiple cycles of plating and filter lifts traditionally required for the isolation of full-length cDNA. Identification of a full length cDNA clone using a partial cDNA as a hybridization probe typically required months of laborious work using traditional library screening techniques, but can be accomplished within a few hours, if a sequence derived from the same partial cDNA is employed as a primer for automated PCR in the method of the invention. The individual bands of amplified cDNA can be eluted from the agarose gel and subcloned without further amplification.

Other features and advantages of the invention will be apparent from the following description of the preferred embodiments thereof, and from the claims.

DESCRIPTION OF THE PREFERRED EMBODIMENTS

The drawings are first described.

DRAWINGS

FIG. 1 is the nucleotide sequence of the 595-base coding strand of CLCP cDNA and the corresponding amino acid sequence of CLCP.

Cloning of gene for CLCP

Figure 2:
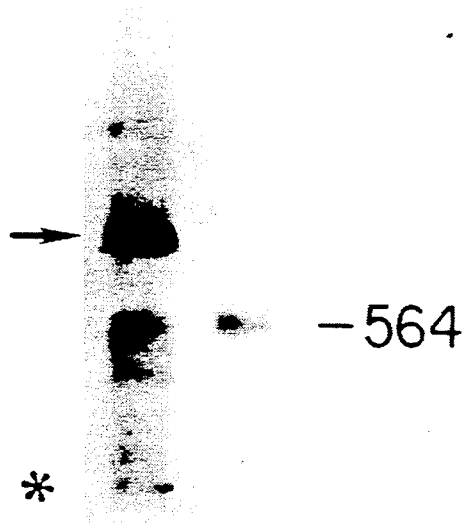
FIG. 2 is a photograph of PCR-amplified CLCP cDNA clones (lane 1) and DNA size markers (lane 2), electrophoresed on 1% agarose gel and stained with ethidium bromide.

A λgt11 library was prepared according to the method of Gubler et al. (Gene 25:263–269, 1983) from poly(A)+ RNA purified from an eosinophil-committed subline of HL-60(3+C-5) (Tomonaga et al., Blood 67:1433–1441, 1986) induced towards eosinophilic differentiation with BCGF-2 (IL 5)(Cellular Products, Inc.).

Expression screening of the oligo-dT-primed λgt11 library with an ELISA employing rabbit polyclonal antisera to reduced and sodium dodecyl sulfate (SDS)-denatured eosinophil CLCP protein identified a partial CLCP cDNA clone (the "primary cDNA clone") containing 299 bases of specific sequence and 3'-poly A tail. In order to obtain a cDNA encoding the full length of CLCP, the following procedure was employed utilizing PCR to amplify selectively those species of CLCP cDNA present in the λgt11 cDNA library:

A single-stranded oligodeoxynucleotide primer (the "specific primer") with the sequence GCTGGCTTGAATCCAAG, corresponding to bases 238 to 222 of the primary cDNA clone s coding strand (bases 509 to 525 of the complete cDNA sequence shown in FIG. 1), was synthesized by standard techniques. Two additional primers (one for each possible insert orientation) were synthesized with sequences respectively corresponding to vector-specified bases 4242–4260 (5'ATGGTAGCGACCGGCGC 3') and 4315–4331 (5'ATCGACGGTTTCCATAT 3') of the E.coli lactose operon flanking the EcoRI insertion site in λgt11 (the "external primers"). Phage DNA from 2 ml of cDNA library stock (titer $10^{10}$ PFU/ml) was purified by standard methods utilizing PEG agglutination of the phage particles, followed by extraction of proteins and resuspension of phage DNA in 100 μl distilled $H_2O$. Each PCR amplification protocol consisted of 20 μM specific primer, 20 μM of one external primer, 10 μl phage DNA, 200 μM dNTPs, 5 μl 10x buffer (100 mM tris pH 8.3, 500 mM KCL, 15 mM $MgCl_2$, 0.1% gelatin), and 1.5U Taq polymerase in total volume 50 μl; primers were annealed at 42° C. and the template amplified for 40 cycles using standard automated PCR techniques in a Perkin Elmer DNA Thermocycler. Five μl of the reaction products were applied to a 1% agarose gel, electrophoresed, and stained with ethidium bromide. As shown in FIG. 2, the PCR products separated on the gel into bands of discrete size, one of which corresponded in size to the initial isolate (marked by an asterisk in FIG. 2). All ethidium-stained bands were shown by Southern blotting to hybridize to denatured DNA from the primary cDNA clone. The DNA in the band representing the longest pieces of amplified DNA, denoted by the arrow in FIG. 2 ("full-length cDNA"), was eluted from the gel and cloned by standard methods into M13 phage in order to facilitate DNA sequencing. Full-length cDNA was found to contain 509 bases 5' to the specific primer. The sequence of CLCP cDNA, including 5'-untranslated and 3' untranslated regions, is shown in FIG. 1. Nucleotides numbered 288 to 595 in FIG. 1 correspond to the sequence of the primary cDNA clone; nucleotides 1 to 525 (including the entire CLCP-encoding-region) correspond to the sequence of PCR-amplified "full length" cDNA. Also shown in FIG. 1 is the amino acid sequence of the polypeptide encoded by the longest open reading frame of the CLCP cDNA sequence, which corresponds to a protein of 142 residues with a molecular weight of 16,247 daltons. This cDNA-deduced amino acid sequence is consistent with the directly-determined (by standard Edman degradation sequencing techniques) 26 residue amino acid sequence of 4 contiguous/overlapping tryptic peptides obtained from purified CLCP extracted from eosinophil granules.

Use

A cloned gene coding for precursor or mature CLCP can be linked by standard cloning methods to appropriate expression control elements on a eukaryotic expression vector and transfected into a chosen cell type to effect CLCP-gene replacement therapy in an organism. Alternatively, CLCP can be produced in cultured cells by cloning the gene onto an appropriate expression vector, which is then introduced into the host cells (such as bacteria, yeast or cultured mammalian cells) using standard techniques. If proper post translational modifications affect activity, a eukaryotic host is preferred. These manipulations are readily accomplished by one of ordinary skill in the field of genetic engineering.

The protein produced by the transformed cells can be purified by standard methods and assayed for lysophospholipase activity by the method of Weller et al., 1984, or for the tendency to form CLC-like dipyramidal crystals under conditions described by Ackerman et al.; Sieker et al., 1988; or Weller et al., 1980, as permitting formation of CLC. The protein product can also be assayed for cross- reactivity to an anti-CLCP or anti-denatured-CLCP antibody in a radiometric or ELISA-based assay.

Purified CLCP can be used to induce production of anti-CLCP antibodies in animals, e.g., rabbits or mice immunized with CLCP by standard methods. The resulting antibodies can be used as in vitro diagnostics, using conventional formats such as ELISA, for disease states characterized by an elevated level of eosinophils: for example, helminthic parasitic infections; asthma and other allergy-related conditions; idiopathic urticaria and atopic dermatitis; idiopathic hypereosinophilic syndrome; and eosinophilic malignancies such as Hodgkin's disease. The body fluid assayed using such antibodies depends on the disease state being diagnosed. For example, in diagnosing asthma, sputum from the lungs or bronchial tree will ordinarily be employed.

Purified CLCP would also have potential therapeutic applications in ameliorating the cytotoxic effects of membrane-disrupting lysophosphatides, such as lysophosphatidyl choline, which are generated in the course of allergic inflammatory reactions. Treatment with CLCP during periods of allergic reactions would convert these toxic lysophosphatides into harmless breakdown products, reducing the severity of cellular damage produced by the inflammation.

Other Embodiments

Other embodiments are within the following claims. For example, a gene encoding CLCP may be obtained by means other than as described above, such as by chemical synthesis in a DNA synthesizer, using the sequence disclosed herein. Alternatively, an oligonucleotide corresponding to a segment of the disclosed DNA sequence can be synthesized, labelled, and used as a probe for the CLCP gene in a genomic DNA library or a cDNA library prepared from human or other animal cells. Genes that code for CLCP need not have exactly the DNA sequence set forth herein: i.e., one can routinely construct (by synthesis, silent mutation or otherwise), or isolate from animal cells, alternative DNA sequences which encode proteins with the precise amino acid sequence of CLCP, but which, owing to the degeneracy of the genetic code, differ by one or more base pairs from the DNA sequence set forth herein. Also within the invention are (1) any DNA sequence which is sufficiently identical to the sequence disclosed herein that it (a) hybridizes to the CLCP sequence disclosed herein, and (b) encodes a polypeptide which cross-reacts with an antibody specific for CLCP or denatured CLCP, which exhibits lysophospholipase activity, or which forms dipyramidal crystals similar to CLC; and (2) any DNA sequence which encodes a polypeptide encoded by a DNA sequence described in (1), but which, owing to the degeneracy of the genetic code, differs from the sequence described in (1) by one or more base pairs.

The gene of the invention may be linked to any of the several expression control sequences known to those skilled in the art, or discovered or developed by known methods, and may be inserted into any known vector/host system.

The method described herein employing PCR to screen a cDNA library could be used to screen virtually any cDNA or genomic DNA library, or several libraries simultaneously, provided that some information is available as to the specific sequence of an appropriate portion of the desired cDNA, such that a first primer can be constructed which, when combined with an appropriate second primer that is based upon vector-specific DNA from a region flanking the cDNA insertion site in the vector, will permit PCR amplification of the intervening cDNA sequence. The sequences from which the two primers are derived must be taken from opposite strands. A primer based upon a DNA sequence that is deduced from a known amino acid sequence would, unless that sequence is at the amino or carboxy terminal of the protein, necessarily result in the amplification of only an incomplete cDNA (encoding only part of the polypeptide), rather than the full-length cDNA obtainable when the primer is based upon a sequence of cDNA outside of the polypeptide-encoding region. The primer, however, could correspond to a sequence which includes some polypeptide-encoding region in addition to flanking untranslated sequence, or it could correspond solely to 3' or 5' untranslated region sequence specific for that cDNA. This sequence information could be obtained as described herein, by isolating a primary cDNA clone that includes some of the sequence adjacent to the 3' poly dA tail. Poly dA or poly dT alone would not be a useful primer for screening clones, as it could provide no specificity to the screen.

The second primer, derived from vector-specific sequence, must be taken from a sequence on the strand of opposite orientation to the strand upon which the first primer's sequence is based. Consistent with the requirements of PCR, each primer must be selected such that DNA synthesis from the annealed primer will proceed in a 5' to 3' direction through the cDNA which is to be amplified. Although the vector based second primer could correspond to vector DNA at any point on the circular molecule that yields a template size which is within the template length limitations of the PCR technique, very long templates are not as efficiently replicated as shorter templates, particularly after several PCR cycles. The sequence of the second primer should be selected to minimize the length of vector DNA included in the template region.

The primers could be designed to add a desired new sequence, such as a restriction site, to one or both ends of the amplified cDNA in order to facilitate subsequent isolation or subcloning of the cDNA.

What is claimed is:

1. A DNA molecule comprising DNA of a plasmid, a phage, or a virus, and a DNA coding sequence selected from the group consisting of:
   (a) the Charcot-Leyden Crystal Protein (CLCP)-encoding sequence shown in FIG. 1;
   (b) a DNA sequence which hybridizes to the CLCP-encoding sequence shown in FIG. 1, and which encodes a polypeptide which (i) cross-reacts with an antibody to CLCP or denatured CLCP, (ii) exhibits lysophospholipase activity, and (iii) forms dipyramidal crystals under conditions permitting CLC formation; and
   (c) a DNA sequence encoding a polypeptide encoded by any of the foregoing DNA sequences.

2. The DNA molecule of claim 1, said recombinant DNA molecule further comprising an expression control sequence operatively linked to said DNA coding sequence.

3. The DNA molecule of claim 1, wherein said DNA coding sequence comprises the CLCP-encoding sequence shown in FIG. 1.

4. A host cell transformed with the DNA molecule of claim 1.

5. The host cell of claim 4, wherein said host cell is selected from the group consisting of strains of *Escherichia coli*, Pseudomonas, Bacillus and fungi, and cultured cells from human, animal or plant tissues.

6. A substantially pure DNA sequence encoding Charcot-Leyden Crystal Protein (CLCP), said DNA sequence being selected from the group consisting of:
   (a) the CLCP-encoding sequence shown in FIG. 1
   (b) a DNA sequence which hybridizes to the CLCP-encoding sequence shown in FIG. 1 and which encodes a polypeptide which (i) cross-reacts with an antibody to CLCP or denatured CLCP, (ii) exhibits lysophospholipase activity, and (iii) forms dipyramidal crystals under conditions permitting CLC formation; and
   (c) a DNA sequence encoding a polypeptide encoded by any of the foregoing DNA sequences.

7. A vector which contains a DNA sequence that encodes Charcot-Leyden Crystal Protein.

8. A method for producing a polypeptide, said method comprising
   (a) providing the recombinant DNA molecule of claim 2,
   (b) transforming a host cell with said recombinant DNA molecule,
   (c) culturing said host cell, and
   (d) collecting said polypeptide.

9. The host cell of claim 8, wherein said host cell is selected from the group consisting of strains of *Escherichia coli*, Pseudomonas, Bacillus, and fungi, and cultured cells from human, animal or plant tissues.

* * * * *